United States Patent [19]

Shvo

[11] Patent Number: 4,465,847

[45] Date of Patent: Aug. 14, 1984

[54] METHOD FOR THE PRODUCTION OF BUTYROLACTONES

[75] Inventor: Youval Shvo, Arsuf, Israel

[73] Assignee: Ramot University Authority for Applied Research and Industry Development Ltd., Tel-Aviv, Israel

[21] Appl. No.: 420,314

[22] Filed: Sep. 20, 1982

[30] Foreign Application Priority Data

Dec. 30, 1981 [IL] Israel .................................... 64677

[51] Int. Cl.$^3$ ........................................... C07D 307/32
[52] U.S. Cl. .................................... 549/295; 549/273
[58] Field of Search ........................................ 549/295

[56] References Cited

PUBLICATIONS

Y. Blum et al., Tetrahedron Letters, vol. 22, No. 16, (1981) pp. 1541-1544.

Shun-Ichi Murahashi et al., Tetrahedron Letters, vol. 22, No. 52, Dec. 11, 1981, pp. 5327-5330.

Youval Shvo et al., Journal of Organometallic Chemistry, vol. 226 (1982) pp. C21-C24.

Primary Examiner—Norma S. Milestone
Attorney, Agent, or Firm—Toren, McGeady and Stanger

[57] ABSTRACT

There is provided a one-step process for the production of diols.

There is provided a process for the conversion of diols in a one-step reaction to polyesters and to lactones, wherein the diols are reacted in the presence of a Group VIII (of the Periodic Table) catalyst with an oxidizing agent, i.e. an agent adapted to remove hydrogen from the reactants, the process being carried out at elevated temperatures. According to a specific embodiment diols having a certain number of carbons are directly converted to lactones, while another embodiment provides for the conversion of but-2-yne-1, 4-diol to butyrolactone.

1 Claim, No Drawings

METHOD FOR THE PRODUCTION OF BUTYROLACTONES

FIELD OF THE INVENTION

There is provided a process for the preparation of polyesters, of certain lactones and of butyrolactone starting with diols, which are reacted in a system comprising certain catalysts, so as to convert same directly to the desired product. Catalysts suitable for the preparation of polyesters and lactones are carbonyls and mixed carbonyls of iron, iridium, osmium, rhenium, ruthenium. Others are certain organic carbonyl compounds. Some of the —CO groups can be replaced by other ligands known in the art, such as trialkyl and triphenyl phosphines, trialkylphosphites, bipyridines, cyclic and acyclic dienes and the like. The homogeneous catalysts for the lactonization of but-2-yne-1,4-diol are metal complexes or salts of transition metals of Group VIII of the Periodic Table. These will be described in detail in the specification.

BACKGROUND OF THE INVENTION

Polyesters and lactones are useful commercial materials which may be prepared by various methods. The starting materials used in some of the known methods are:
1. Diols + dicarboxylic acids;
2. Diols + anhydrides of dicarboxylic acids;
3. Diols + dichlorides of dicarboxylic acids;
4. Diols + esters of dicarboxylic acids;
5. Lactones;
6. Hydroxy carboxylic acids;

Usually the synthesis of dicarboxylic acids, anhydrides, dichlorides and esters require the oxidation of diols according to the following scheme:

$$HOCH_2(CH_2)_nCH_2OH \xrightarrow{[O]} HO_2C(CH_2)_nCO_2H \begin{Bmatrix} \to \text{Anhydrides} \\ \to \text{Dichlorides} \\ \to \text{Esters} \end{Bmatrix} \xrightarrow{\text{Diol}} \text{Polyesters}$$

Thus, diols serve as chemical precursors for the preparation of dicarboxylic acid, their anhydrides, dichlorides and esters which then in conjunction with the diols yield the desired polyesters by known methods.

SUMMARY OF THE INVENTION

According to one aspect of the invention there is provided a process for the direct conversion of diols to polyesters. According to a modification of this process, certain diols are directly converted to lactones. Yet a further modification of the process relates to the direct conversion of but-2-yne-1,4-diol to butyrolactone.

The reactions are effected at elevated temperature in the presence of specific catalysts, which will be defined in detail in the following.

The general reaction scheme for the preparation of polyesters from diols in a direct one-step reaction is as follows:

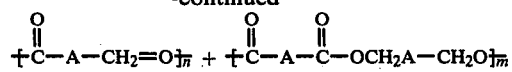

where I and II designate recurring moieties which occur in the polymer and wherein A designates a bivalent aliphatic, aromatic, alkylanomatic or heterocyclic group which may carry one or more O,N,P,S or halogen atoms, which A group can be interrupted by one or more oxygen, sulfur, nitrogen or phosphorus atoms. Preferred diols are alkylene glycols such as ethylene glycol, propylene glycol or various isomers of phthaloyl glycols.

The process of the invention comprises converting such diols or substituted diols directly to polyesters by contacting same with an "oxidizing agent", as herein defined, in the presence of a specific catalyst, preferably under an inert atmosphere at an elevated temperature in the range of about 50° to 200° C., and preferably at about 120°-170° C. The resulting polymer is purified by conventional means after completion of the reaction.

Amongst "oxidizing agents" suitable for the process of the present invention there are agents adapted to abstract hydrogens expelled from the diols from the reaction mixture. Any organic or inorganic compound which will fulfil this function is suitable, and amongst these there may be mentioned olefinic compounds, and especially such olefins which have double bonds conjugated with carbonyl groups or with other electron withdrawing groups; acetylenic compounds; oxygen (in which case no inert atmosphere need be used); organic nitro, cyano and imino compounds; certain polyhalogenated alkanes and preferably carbon tetrachloride and CnO.

The reaction can be carried out without or with a suitable solvent. Such solvents are used in order to facilitate the handling of the reactants and products; solvents with boiling points close to the temperature of the reaction being preferred. The reactants and products ought to be soluble in the solvent. Primary and secondary alcohols as well as keto, ester and amino compounds are generally not suitable as solvents.

A specific embodiment of the invention relates to the direct conversion of diols to lactones. Diols with an appropriate number of carbon atoms, when subjected to reaction conditions as defined above, are directly converted to lactones as set out in the following reaction scheme:

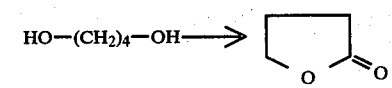

HO—(CH$_2$)$_5$—OH ⟶ 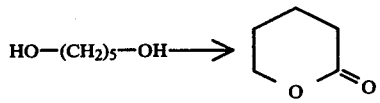

It is known that 5- and 6-membered ring lactones are of high stability and that such lactones form readily. Thus, preferred products of this reaction are various unsubstituted and substituted butyrolactones and valerolactones.

A further embodiment of the process of the present invention relates to the direct conversion of but-2-yne-1,4-diol to butyrolactone by treatment with a suitable catalyst under conditions of reaction as defined above. No addition of oxidizing agent is required as the triple bond of the starting compound fulfills this function. This ought to be contrasted with the conventional two-step process of hydrogenation of but-2-yne-1,4-diol to butanediol, followed by oxidation to butyrolactone, which requires hydrogen, two moles of which are lost.

The molar ratio of catalyst to diol is about 1:10 to 1:500, the preferred ratio being about 1:100 to 1:300. The preferred molar ratio of oxidizing agent to diol is about 1:1 to about 3:1. When the reaction is carried out in the presence of a solvent, the solvent is used in a weight ratio of from 2:1 to about 10:1, respective the diol.

The catalysts for the process of the invention for the production of polyesters and lactones are preferably homogeneous catalysts based mainly on Group VIII metals selected from iron, iridium, osmium, rhodium and ruthenium, such as the carbonyl derivatives of these. The most preferred catalysts are those based on osmium and ruthenium, and these can be used in the form of complexes and salts; some of the CO groups of the compounds can be replaced by ligands such as trialkyl and triphenyl phosphines, trialkylphosphites, bipyridines, cyclic and acyclic dienes etc. Amongst specific compounds which are suitable as catalysts there may be mentioned:

Fe$_3$(CO)$_{12}$
Ir$_4$(CO)$_{12}$
Os$_3$(CO)$_{12}$
Rh$_6$(CO)$_{16}$
Ru$_3$(CO)$_{12}$
H$_2$Ru$_4$(CO)$_{12}$
[(PhCO$_2$)(CO)$_3$Ru]$_2$
Fe$_3$(CO)$_{12}$/Ru$_3$(CO)$_{12}$
Os$_3$(CO)$_{12}$/Rh$_6$(CO)$_{16}$
Ru$_3$(CO)$_{12}$/Ir$_4$(CO)$_{12}$ etc.

For the lactonization of but-2-yne-1,4-diol compounds defined above can be used; preferred catalysts for this specific reaction being catalysts listed hereinafter and complexes of these with modifying ligands such as carbon monoxide, triphenyl and trialkyl phosphines, arsine, bipyridines and dienes. Some of the suitable compounds are metal complexes of salts of transition metals from group VIII of the periodic table. Ruthenium, rhodium and iridium complexes are recommended. The catalysts comprise a group of complexes having a usual modifying ligands known in the art viz. carbon monoxide, triphenyl and trialkyl phosphines and arsine, hydrogen, halogens, bipyridines and dienes. Some examples are presented in the following list:

RuCl$_2$(PPh$_3$)$_3$
RuH$_2$(PPh$_3$)$_4$
RuH$_2$(CO)(PPh$_3$)$_3$
RuHCl(CO)[P(C$_6$H$_{11}$)$_3$]$_3$
RuCl$_3$
RhCl(PPh$_3$)$_3$
RhH(PPh$_3$)$_4$
Rh(1,5-COD)(PR$_3$)Cl
IrCl(CO)(PPh$_3$)$_2$
Ir(Bipyridine)(1,5-COD)Cl Polymetal complexes also known as clusters were found to possess catalytic activity. Some examples are listed below:

Ru$_3$(CO)$_{12}$, Os$_3$(CO)$_{12}$, Fe$_3$(CO)$_{12}$, H$_2$Ru$_4$(CO)$_{12}$.

The ligands of these catalysts can also be modified as was previously described.

The following examples illustrate the invention, and these are illustrative only and not restrictive.

EXAMPLE 1

Preparation of Polyester 11.8 g 1,6-hexanediol, 0.32 g dodecarbonyltriruthenium, 36.4 g diphenylacetylene and 20 g diglyme were placed in an autoclave under a blanket of nitrogen. The mixture was heated for 5 hours at 150°. The solvent was removed by vacuum distillation and the residue was extracted with petroleum ether. A solid polymer was obtained upon mild drying, 8.7 g.

EXAMPLE 2

Preparation of Butyrolactone 9.0 g 1,4-butanediol 0.7 g dodecacarbonyl dihydridotetraruthenium and 21 g chalcone were placed in an autoclave under a blanket of nitrogen. The mixture was heated for a period of 4 hours at 150°. Butyrolactone, 6.1 g, was obtained by vacuum distillation. The ruthenium could be recovered from the distillation residue by known methods.

EXAMPLE 3

Production of Butyrolactone 8.6 g but-2-yne-1,4-diol and 1.1 g dihydrido tetrakis-triphenylphosphine ruthenium were placed in an autoclave under a blanket of nitrogen. The mixture was heated for 3 hours at 140°. Butyrolactone, 4.3 g, was obtained by distilling the reaction mixture.

Examples were carried out with different starting compounds, and these gave results as indicated in the reaction scheme set out in the general description.

I claim:

1. A process for the production of butyrolactone comprising heating but-2-yne-1,4-diol at a temperature in the range from 50° to 200° C. in the presence of a catalyst selected from the group consisting of
RuCl$_2$(PPh$_3$)$_3$,
RuH$_2$(PPh$_3$)$_4$,
RuH$_2$(CO)(PPh$_3$)$_3$,
RuHCl(CO)[P(C$_6$H$_{11}$)$_3$]$_3$,
RuCl$_3$,
RhCl(PPh$_3$)$_3$,
RhH(PPh$_3$)$_4$,
IrCl(CO)(PPh$_3$)$_2$, and
Ir(Bipyridine)(1,5-COD)Cl,
wherein Ph designates phenyl, and COD designates cyclooctadiene.

* * * * *